(12) United States Patent
Chin et al.

(10) Patent No.: US 9,162,028 B2
(45) Date of Patent: Oct. 20, 2015

(54) SYRINGE FOR TREATING FACIAL WRINKLES AND OPERATION METHOD USING THE SAME

(75) Inventors: Sae Hoon Chin, Sungnam-si (KR); Joong Suk Jin, Sungnam-si (KR); Jin Sik Burm, Seoul (KR)

(73) Assignees: Sae Hoon Chin, Sungnam-Si (KR); Joong Suk Jin, Sungnam-Si (KR)

( * ) Notice: Subject to any disclaimer, the term of this patent is extended or adjusted under 35 U.S.C. 154(b) by 604 days.

(21) Appl. No.: 13/014,076

(22) Filed: Jan. 26, 2011

(65) Prior Publication Data

US 2012/0191036 A1    Jul. 26, 2012

(51) Int. Cl.
*A61M 5/00* (2006.01)
*A61M 5/20* (2006.01)
*A61M 5/31* (2006.01)

(52) U.S. Cl.
CPC ............... *A61M 5/204* (2013.01); *A61M 5/31* (2013.01); *A61M 2005/3128* (2013.01); *A61M 2202/0007* (2013.01); *A61M 2202/02* (2013.01); *A61M 2210/04* (2013.01)

(58) Field of Classification Search
CPC ............. A61M 2005/006; A61M 5/16822; A61M 2005/1787; A61M 2005/3128; A61M 5/3134; A61M 5/3148; A61M 5/3293; A61M 5/31531; A61M 2025/0042; A61M 37/0015; A61M 2037/0023; A61M 2037/003; A61M 2037/0038; A61M 2037/0061
USPC ......................................................... 604/247
See application file for complete search history.

(56) References Cited

U.S. PATENT DOCUMENTS

| 3,572,375 | A | * | 3/1971 | Rosenberg | .................... | 137/512 |
| 4,838,866 | A | * | 6/1989 | Marshall, Sr. | ................ | 604/152 |
| 6,569,143 | B2 | * | 5/2003 | Alchas et al. | ................. | 604/506 |
| 2004/0182887 | A1 | | 9/2004 | Sugimura et al. | | |
| 2005/0074501 | A1 | | 4/2005 | Murphy et al. | | |
| 2008/0114295 | A1 | * | 5/2008 | Glynn | ........................... | 604/110 |
| 2009/0124996 | A1 | * | 5/2009 | Heneveld et al. | ............. | 604/506 |

* cited by examiner

*Primary Examiner* — Aarti B Berdichevsky
*Assistant Examiner* — Laura Schell
(74) *Attorney, Agent, or Firm* — The Webb Law Firm

(57) ABSTRACT

The present invention relates to a syringe for treating facial wrinkles having a syringe cylinder, a needle body detachably mounted at the front end portion of the syringe cylinder and having a syringe needle disposed thereon, and a piston rod disposed inside the syringe cylinder for operating a piston, the syringe including: the syringe cylinder formed of a substantially thin tube having an inside diameter in a range of 2.0 mm to 7.0 mm; and an inflow check valve disposed at one side of the front end portion of the syringe cylinder so as to supply a predetermined quantity of gas to the interior of the syringe cylinder, wherein the predetermined quantity of gas supplied through the inflow check valve to the interior of the syringe cylinder and a predetermined quantity of liquid filled into the syringe cylinder are injected in turn into the dermis of the skin, which is repeatedly carried out.

5 Claims, 11 Drawing Sheets

SYRINGE FOR TREATING FACIAL WRINKLES AND OPERATION METHOD USING THE SAME

BACKGROUND OF THE INVENTION

1. Field of the Invention

The present invention relates to a syringe for treating facial wrinkles and an operation method using the syringe, and more particularly, to a syringe for treating facial wrinkles and an operation method using the syringe wherein a desired quantity of gas is first injected into a layer of skin (which is hereinafter referred to as 'dermis') between the epidermis and the subcutaneous tissues, without giving any injury to the epidermis, and a desired quantity of liquid is then injected into the space of the dermis expanded easily by the injected gas, which is repeatedly carried out.

2. Background of the Related Art

Generally, the dermis is located between the epidermis and the subcutaneous tissues of the skin of the vertebrate, which is formed from the mesoderm and is composed of fibrous connective tissues having a thickness of 0.3 mm to 2.4 mm. The dermis includes sweat glands, hair follicles, sebaceous glands and the like, from which all of the biological functions of the skin occur.

As a conventional method for treating facial wrinkles, there has been provided a dermal rejuvenation method that allows the epidermis of the facial skin covering the dermis to be injured so as to perform the dermal rejuvenation, which includes mechanical dermabrasion, laser peeling, chemical peeling, cryosurgery and the like. However, these methods have the following disadvantages: firstly, a period of time required for treatment and recovery is relatively long (for example, about 1 to 2 years); secondly, in case of people of color, especially, hyperpigmentation and hypopigmentation may be found on them; and lastly, it is hard to easily select these treatment methods because of complication like the formation of severe irregular scars.

SUMMARY OF THE INVENTION

Accordingly, the present invention has been made in view of the above-mentioned problems occurring in the prior art, and it is an object of the present invention to provide a syringe for treating facial wrinkles wherein a desired quantity of gas is first injected into the dermis of the facial skin and a desired quantity of liquid is then injected into the dermis of the facial skin expanded easily by the injected gas, which is repeatedly carried out.

To accomplish the above object, according to an aspect of the present invention, there is provided a syringe for treating facial wrinkles having a syringe cylinder, a needle body detachably mounted at the front end portion of the syringe cylinder and having a syringe needle disposed thereon, and a piston rod disposed inside the syringe cylinder for operating a piston, the syringe including: the syringe cylinder formed of a substantially thin tube having an inside diameter in a range of 2.0 mm to 7.0 mm; and an inflow check valve disposed at one side of the front end portion of the syringe cylinder so as to supply a predetermined quantity of gas to the interior of the syringe cylinder, wherein the predetermined quantity of gas supplied through the inflow check valve to the interior of the syringe cylinder and a predetermined quantity of liquid filled into the syringe cylinder are injected in turn into the dermis of the skin, which is repeatedly carried out.

According to the present invention, preferably, the syringe for treating facial wrinkles further includes an outflow check valve disposed between the front end portion of the syringe cylinder and the needle body.

According to the present invention, preferably, the syringe cylinder has another syringe cylinder disposed integrally around the lower periphery thereof in such a manner as to have a larger inside diameter than the syringe cylinder.

To accomplish the above object, according to another aspect of the present invention, there is provided a syringe for treating facial wrinkles having a syringe cylinder, a needle body detachably mounted at the front end portion of the syringe cylinder and having a syringe needle disposed thereon, and a piston rod disposed inside the syringe cylinder for operating a piston, the syringe including: the needle body having an inside diameter in a range of 2.0 mm to 7.0 mm; and an inflow check valve disposed at one side of the needle body so as to supply a predetermined quantity of gas to the interior of the needle body, wherein the predetermined quantity of gas supplied through the inflow check valve to the interior of the needle body and a predetermined quantity of liquid filled into the syringe cylinder are injected in turn into the dermis of the skin, which is repeatedly carried out.

To accomplish the above object, according to still another aspect of the present invention, there is provided an operation method using a syringe including the steps of: injecting gas into the lower dermis and the reticular layer in the lower dermis giving important influences on skin elasticity and wrinkles and forming an expanded space thereinto through the large penetration of the gas into the skin tissues, thereby inducing first collagen regeneration through the injury of the skin tissues caused during the diffusion of the gas; inducing chemical injury through the difference between the pH (in case of $CO_2$, pH2 to pH3, and in case of $NH_3$, pH11 to pH12) of the injected gas and the pH (about 7.4) of a normal body fluid, thereby inducing second collagen regeneration; filling hyaluronic acid into the expanded space to add the hyaluronic acid needed on the aged dermis, thereby obtaining third collagen regeneration, whereby the three-time tissue regeneration is continuously performed at a time.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Figure 1:
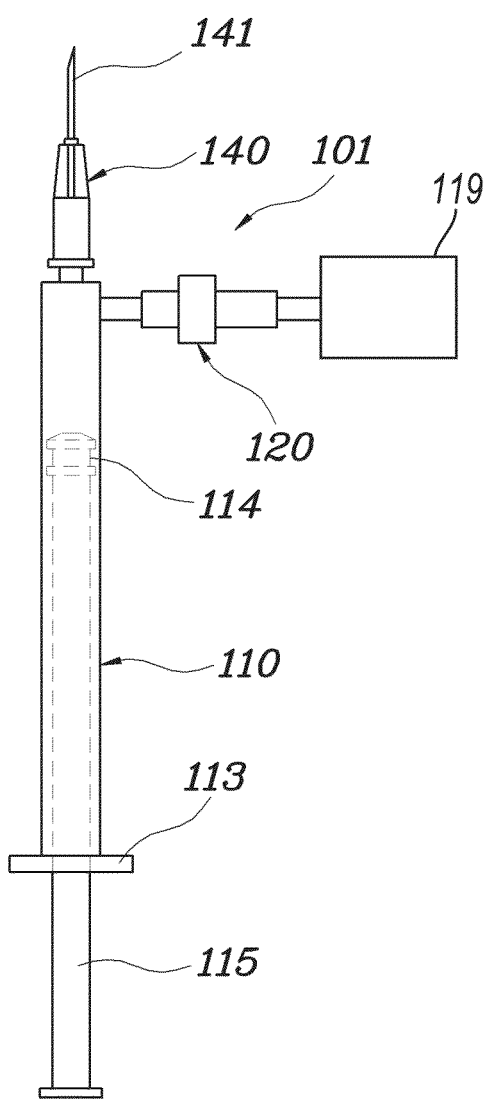
FIG. 1 is a side view showing a syringe for treating facial wrinkles according to a first embodiment of the present invention.

Injecting gas like carbonic acid gas or ammonia causes the dermis to be partially isolated and injured, which allows the injection of a liquid into the dermis to be easier and also enables the partial isolation of the dermis to be carried out in a more expanded range. In this case, fibrin is formed on the region where the dermis is injured, such that the skin becomes thick, contracted and aged, and thus, the aged skin having low elasticity and the dermis having a low thickness can be rejuvenated.

Especially, carbonic acid gas ($CO_2$) is combined with water in the human body to form carbonic acid and exhibit a mildly acidic property of about pH3, as shown in the following chemical equation.

$$CO_2 + H_2O \rightarrow H_2CO_3 \leftrightarrow H^+ + HCO_3^-$$

In the meantime, ammonia responds to water to form ammonium hydroxide and is dissociated to form hydroxyl group, thereby exhibiting a mildly alkaline property of about pH11, as shown in the following chemical equation.

$$NH_3 + H_2O \rightarrow NH_4OH \leftrightarrow NH_4^+ + OH^-$$

The mild acid or mild alkali liquid formed by the injection of the carbonic acid gas or ammonia enables the tissues in the space of the partially isolated dermis to be stimulated to cause light chemical burn thereon, thereby obtaining more excellent effects in the rejuvenation of the collagen fibers of the dermis.

Then, if water, hyaluronic acid dissolved into water, or an aqueous solution of collagen is injected into the dermis, the dermis becomes thick, such that the isolated space is maintained for a long period of time by means of the injected gas. Further, the secretion of body fluids becomes accelerated and the production of fibers becomes dynamically induced, thereby removing wrinkles on the skin and giving elasticity on the skin. Also, the injection of carbonic acid gas ($CO_2$) provides skin whitening effects.

In the above-mentioned processes, the gas is injected into the dermis and the liquid should be injected into the same position as where the gas is injected. At the time of injection, a syringe should be erected on the skin, and if a piston rod is moved backwardly from the syringe into which the liquid is filled, gas is supplied to the interior of a syringe cylinder. At this time, if the syringe is erected, the gas is light and rises over the liquid, thereby causing reverse flow therein. Before the injection of the liquid, accordingly, the gas cannot be first injected with existing syringes.

The present inventor has made various studies to solve the above problem and as a result, he has found that if the syringe cylinder of the syringe has an inside diameter of less than 7.0 mm, gas is supplied below a liquid filled into the syringe cylinder by means of the surface tense of the liquid, and thus, even if the syringe is erected, the gas does not rise over the liquid and still remains below the liquid, thereby preventing the reverse flow of the gas. The smaller the inside diameter of the syringe cylinder of the syringe becomes, the better the above-mentioned effect becomes. If the inside diameter of the syringe cylinder is too small, quantities of liquid and gas to be injected become reduced. Accordingly, it is desirable that the inside diameter of the syringe cylinder is in a range of 2.0 mm to 7.0 mm.

Next, an explanation on a syringe for treating facial wrinkles according to preferred embodiments of the present invention will be in detail given with reference to the attached drawings.

FIG. 1 is a side view showing a syringe for treating facial wrinkles according to a first embodiment of the present invention, wherein a body 101 of the syringe for treating facial wrinkles includes a syringe cylinder 110 formed of a substantially thin tube having an inside diameter in a range of 2.0 mm to 7.0 mm, a needle body 140 detachably mounted on the front end portion of the syringe cylinder 110 and having a syringe needle 141 disposed thereon, a piston rod 115 disposed in the interior of the syringe cylinder 110 for operating a piston 114, and an inflow check valve 120 disposed at one side of the front end portion of the syringe cylinder 110 and connected to a gas supply 119. The inflow check valve 120, which is adopted in the present invention, is well known to those skilled in the art.

Figure 2:
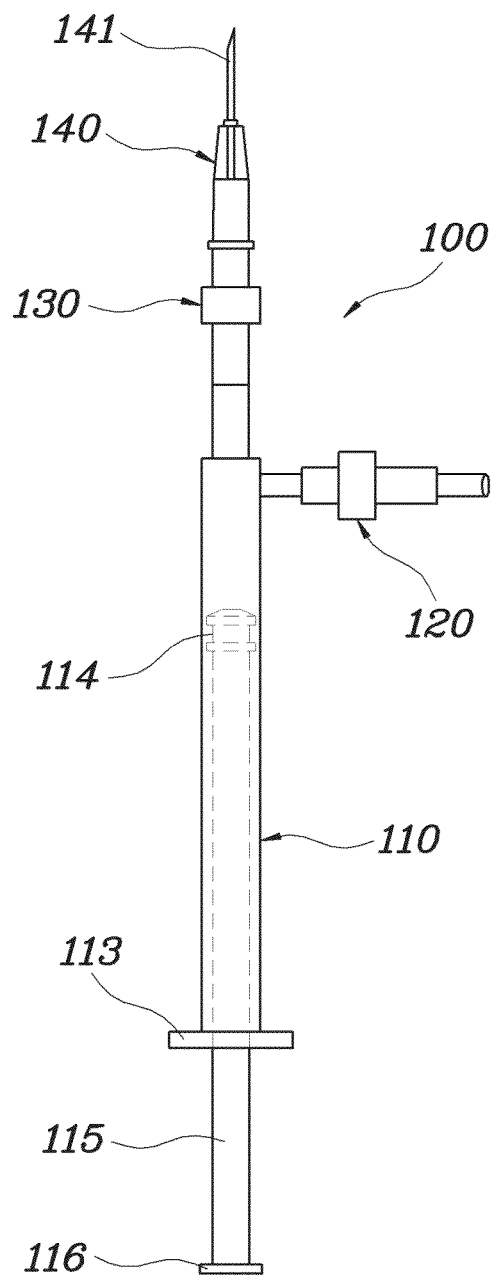
FIG. 2 is a side view showing a syringe for treating facial wrinkles according to a second embodiment of the present invention.

FIG. 2 is a side view showing a syringe for treating facial wrinkles according to a second embodiment of the present invention, wherein a body 100 of the syringe for treating facial wrinkles includes a syringe cylinder 110 formed of a substantially thin tube having an inside diameter in a range of 2.0 mm to 7.0 mm, a needle body 140 having a syringe needle 141 disposed thereon, an outflow check valve 130 disposed between the front end portion of the syringe cylinder 110 and the needle body 140, a piston rod 115 disposed in the interior of the syringe cylinder 110 for operating a piston 114, and an inflow check valve 120 disposed at one side of the front end portion of the syringe cylinder 110.

Figure 3:
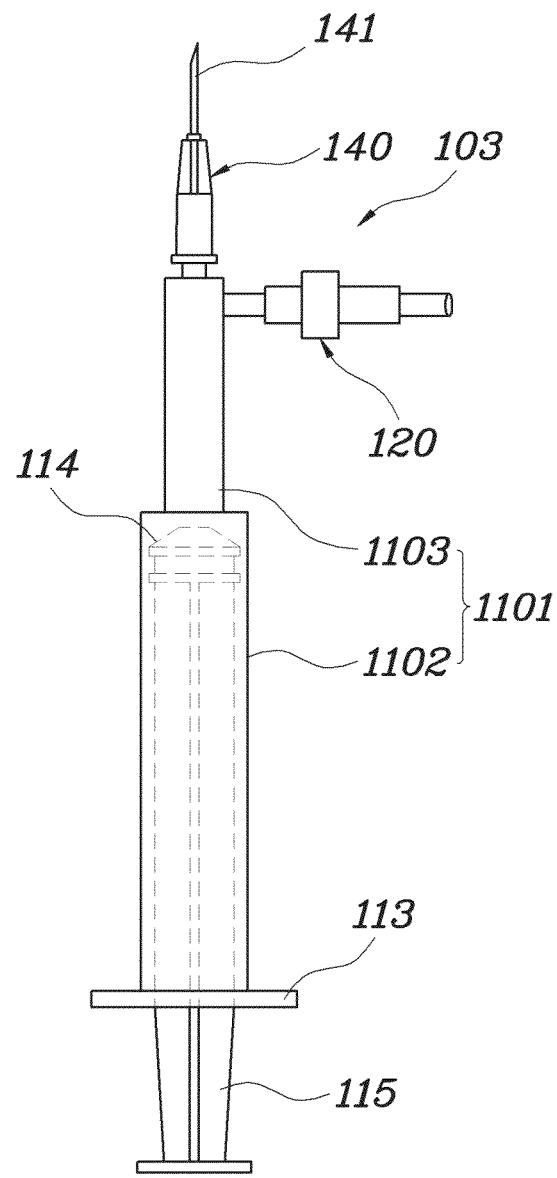
FIG. 3 is a side view showing a syringe for treating facial wrinkles according to a third embodiment of the present invention.

FIG. 3 is a side view showing a syringe for treating facial wrinkles according to a third embodiment of the present invention, wherein a body 103 of the syringe for treating facial wrinkles includes a syringe cylinder 1101 having a first syringe cylinder 1103 formed of a substantially thin tube having an inside diameter in a range of 2.0 mm to 7.0 mm and a second syringe cylinder 1102 like a typical syringe cylinder having a relatively large inside diameter and formed integrally to the first syringe cylinder 1103 in such a manner as to be disposed concentrically above the outer periphery of the first syringe cylinder 1103, a needle body 140 detachably mounted on the front end portion of the first syringe cylinder 1103 and having a syringe needle 141 disposed thereon, a piston rod 115 disposed in the interior of the second syringe cylinder 1102 for operating a piston 114, and an inflow check valve 120 disposed at one side of the front end portion of the first syringe cylinder 1103.

Figure 4:
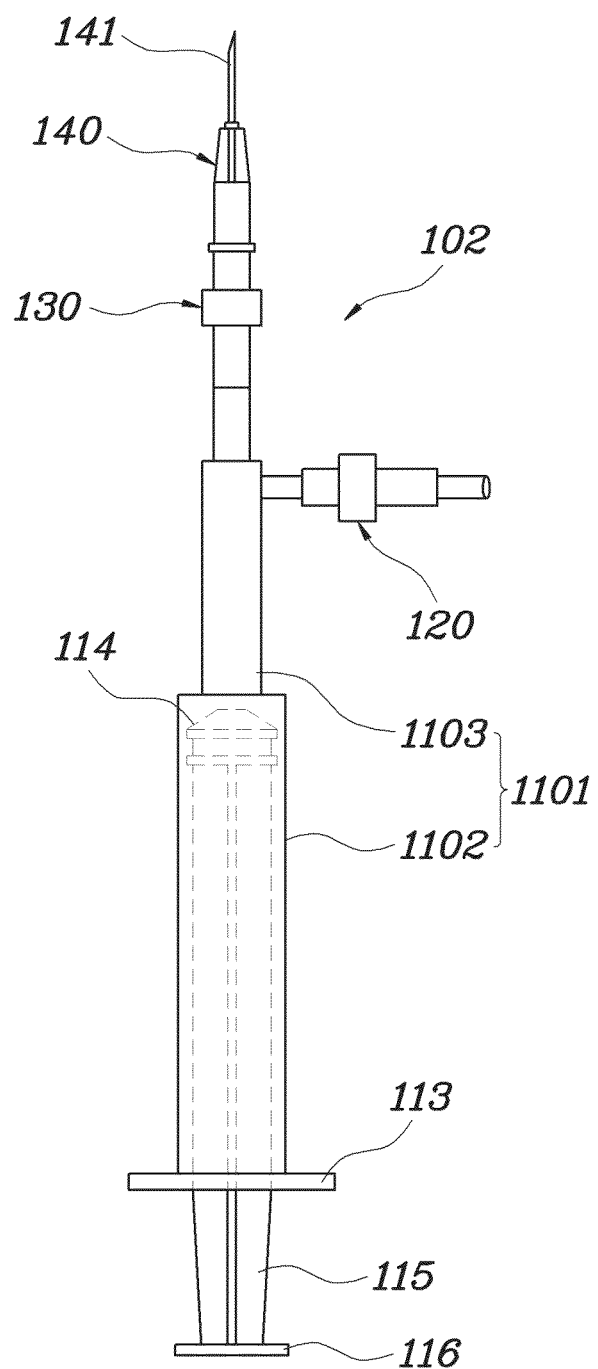
FIG. 4 is a side view showing a syringe for treating facial wrinkles according to a fourth embodiment of the present invention.

FIG. 4 is a side view showing a syringe for treating facial wrinkles according to a fourth embodiment of the present invention, wherein a body 102 of the syringe for treating facial wrinkles includes a syringe cylinder 1101 having a first syringe cylinder 1103 formed of a substantially thin tube having an inside diameter in a range of 2.0 mm to 7.0 mm and a second syringe cylinder 1102 like a typical syringe cylinder having a relatively large inside diameter and formed integrally to the first syringe cylinder 1103 in such a manner as to be disposed concentrically above the outer periphery of the first syringe cylinder 1103, an outflow check valve 130 disposed between the front end portion of the first syringe cylinder 1103 and a needle body 140, a piston rod 115 disposed in the interior of the second syringe cylinder 1102 for operating a piston 114, and an inflow check valve 120 disposed at one side of the front end portion of the first syringe cylinder 1103.

Figure 6:
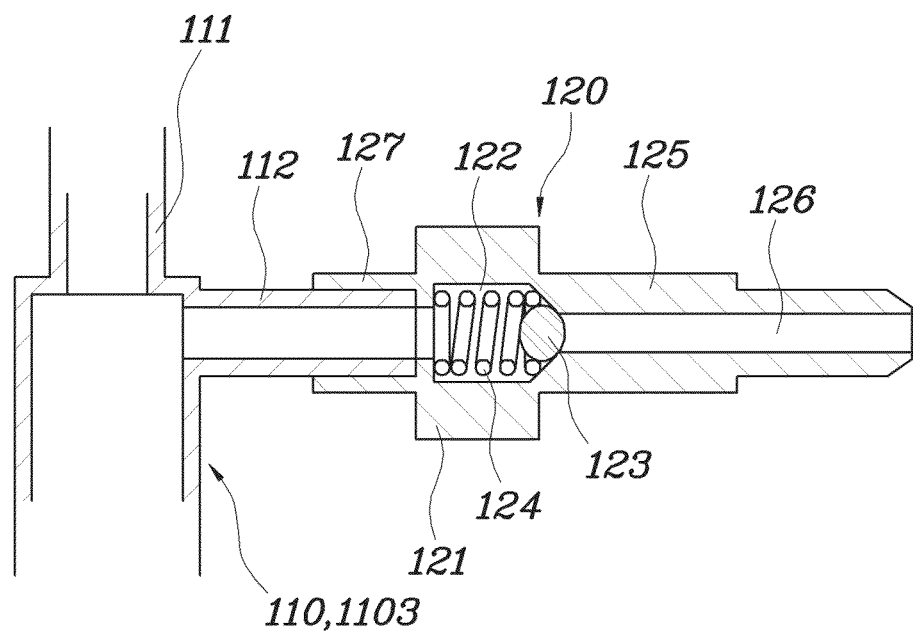
FIG. 6 is a sectional view showing an inflow check valve in the syringe for treating facial wrinkles according to the present invention.

As shown in FIG. 6, the inflow check valve 120 is disposed on a connection tube 112 located perpendicularly to one side of the front end portion of the syringe cylinder 110 or the first syringe cylinder 1103 and includes a connection portion 127 coupled to the connection tube 112, a housing 121, and an inflow tube 125 sequentially located concentrically with respect to one another.

The housing 121 has a receiving space 122 formed therein, and the receiving space 122 has a spring 124 and a valve 123 mounted therein. The inflow tube 125 has an inflow passageway 126 formed along the center thereof, and the valve 123 serves to block the inflow passageway 126 of the inflow tube 125 by means of the elasticity of the spring 124.

Figure 5:
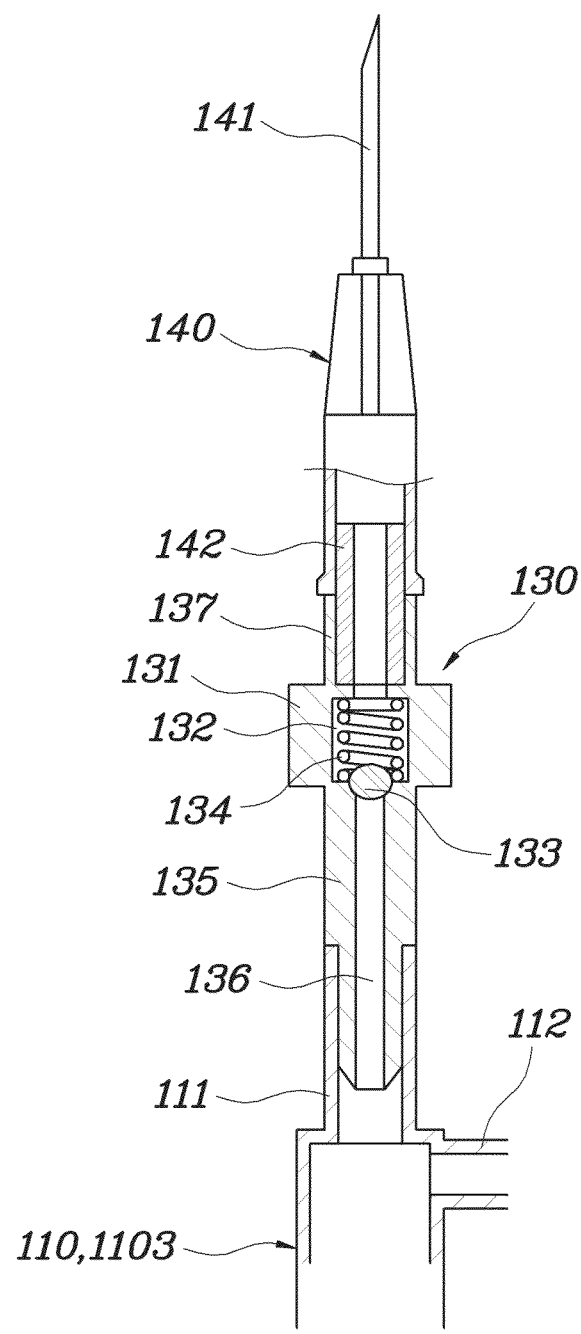
FIG. 5 is a sectional view showing an outflow check valve in the syringe for treating facial wrinkles according to the present invention.

As shown in FIG. 5, the outflow check valve 130 is disposed on a connection tube 111 located concentrically at the front end portion of the syringe cylinder 110 or the first syringe cylinder 1103 and includes a discharge tube 135 coupled to the connection tube 111, a housing 131, and a connection portion 137 sequentially located concentrically to one another.

The housing 131 has a receiving space 132 formed therein, and the receiving space 132 has a spring 134 and a valve 133 mounted therein. The discharge tube 135 has a discharge passageway 136 formed along the center thereof, and the valve 133 serves to block the discharge passageway 136 of the discharge tube 135 by means of the elasticity of the spring 134.

The connection portion 137 is coupled along the inner periphery thereof concentrically to the lower portion of a syringe needle-mounting tube 142, and the needle body 140 having the syringe needle 141 disposed thereon is coupled to the upper portion of the syringe needle-mounting tube 142.

Figure 7:
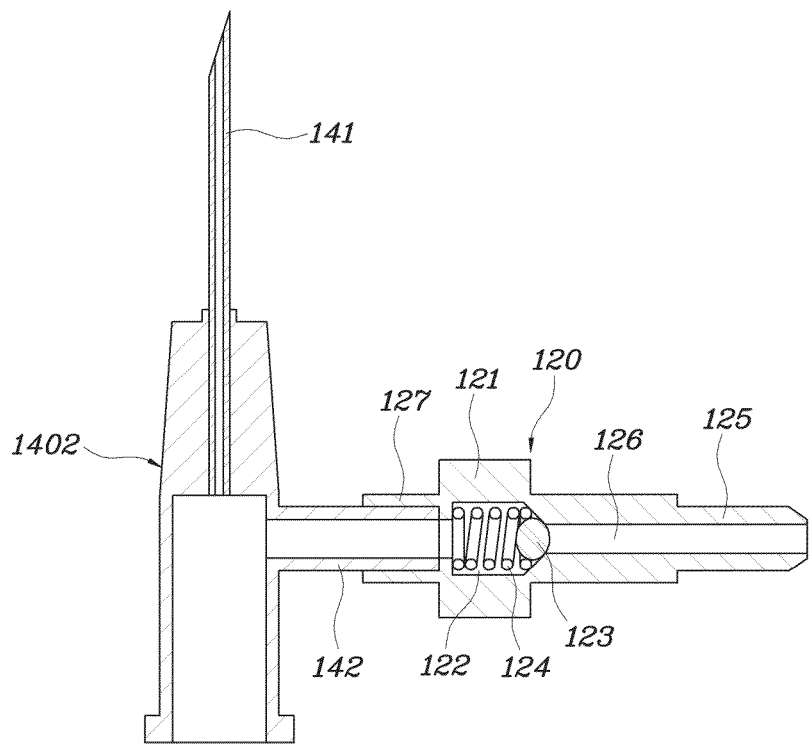
FIG. 7 is a sectional view showing a needle body in a syringe for treating facial wrinkles according to a fifth embodiment of the present invention.

FIG. 7 is a sectional view showing a needle body in a syringe for treating facial wrinkles according to a fifth embodiment of the present invention, wherein a needle body 1402 has an inflow check valve 120 disposed at one side thereof and an inside diameter in a range of 2.0 mm to 7.0 mm, thereby performing the functions of the syringe cylinder as mentioned above.

In this case, the inflow check valve 120 is disposed on a connection tube 142 located perpendicularly to one side of the needle body 1402 and includes the connection portion 127 coupled to the connection tube 142, the housing 121, and the inflow tube 125 sequentially located concentrically with respect to one another.

The housing 121 has the receiving space 122 formed therein, and the receiving space 122 has the spring 124 and the valve 123 mounted therein. The inflow tube 125 has the inflow passageway 126 formed along the center thereof, and the valve 123 serves to block the inflow passageway 126 of the inflow tube 125 by means of the elasticity of the spring 124.

Figure 8:
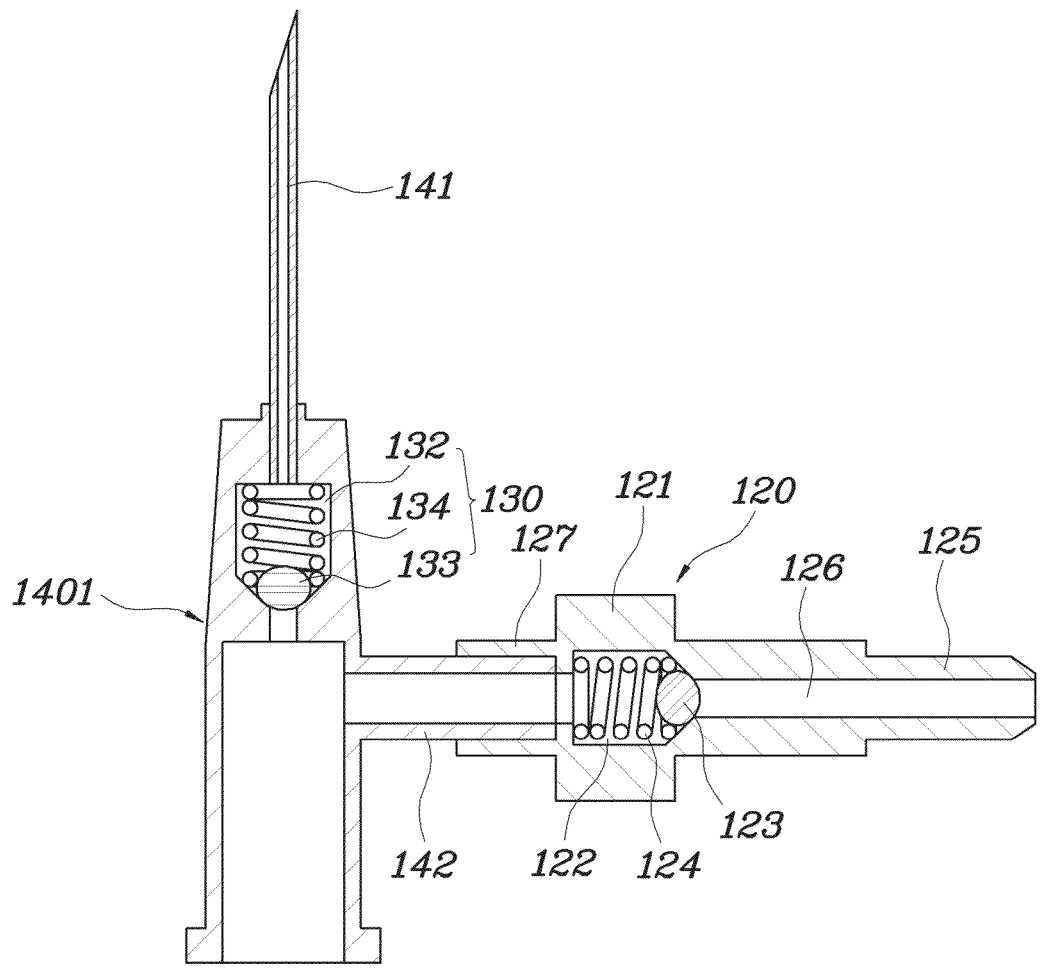
FIG. 8 is a sectional view showing a needle body in a syringe for treating facial wrinkles according to a sixth embodiment of the present invention.
Figure 9:
FIG. 9 is a photograph showing glabella winkle before operation.
Figure 10:
FIG. 10 is a photograph showing glabella winkle after operation of the present invention.
Figure 11:
FIG. 11 is a photograph showing winkle of left cheek around oral commissure before operation.
Figure 12:
FIG. 12 is a photograph showing winkle of left cheek around oral commissure after operation of the present invention.
Figure 13:
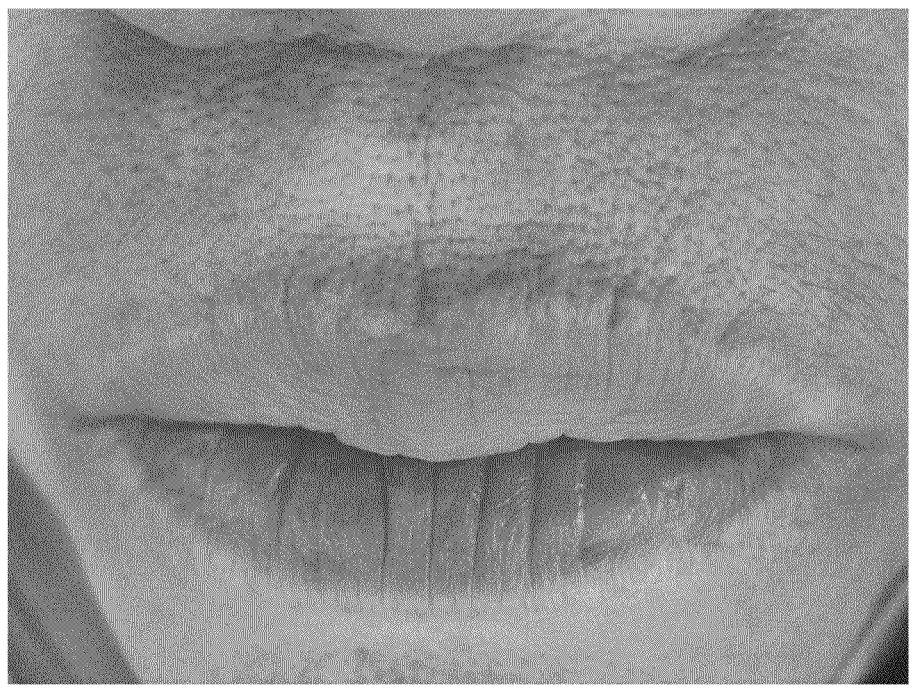
FIG. 13 is a photograph showing winkle of upper lip before operation.
Figure 14:
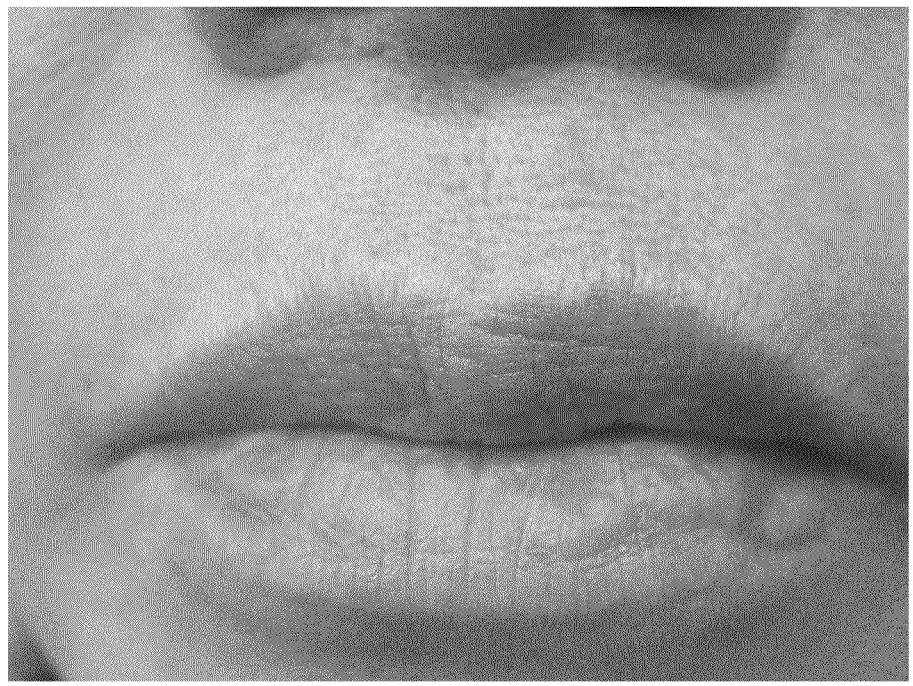
FIG. 14 is a photograph showing winkle of upper lip after operation of the present invention.
Figure 15:
FIG. 15 is a photograph showing mentum winkle of mandible body area before operation.
Figure 16:
FIG. 16 is a photograph showing mentum winkle of mandible body area after operation of the present invention.

FIG. 8 is a sectional view showing a needle body in a syringe for treating facial wrinkles according to a sixth embodiment of the present invention, wherein a needle body 1401 has the receiving space 132 formed at the front end portion thereof, and the receiving space 132 has the spring 134 and the valve 133 mounted therein. The valve 133 blocks the passageway formed between the interior of the needle body 1401 and the syringe needle 141 by means of the elasticity of the spring 134.

The syringe cylinders of the syringe of the present invention may have graduations for indicating quantities of gas or liquid thereon, thereby measuring the quantity of gas or liquid to be injected into the dermis.

Hereinafter, an explanation on the operation methods using the syringes for treating facial wrinkles according to the preferred embodiments of the present invention will be given.

Firstly, according to the first embodiment of the present invention as shown in FIG. 1, an operation method using the syringe for treating facial wrinkles includes the steps of: a) filling a predetermined quantity of liquid into the syringe cylinder 110; b) putting the syringe needle 141 into the dermis of the skin; c) pulling the piston rod 115 to allow a desired quantity of gas to be supplied to the interior of the syringe cylinder 110 through the inflow passageway 126 of the inflow tube 125, such that the desired quantity of gas exists in the front end portion of the syringe cylinder 110 and the liquid filled into the syringe cylinder 110 is placed below the desired quantity of gas; and d) pushing the piston rod 115 to first inject the desired quantity of gas into the dermis and to then inject a desired quantity of liquid into the dermis, wherein the steps c) and d) are repeatedly carried out to allow the gas and liquid to be injected by desired quantities in turn into the dermis.

Secondly, according to the second embodiment of the present invention as shown in FIG. 2, an operation method using the syringe for treating facial wrinkles includes the steps of: a) filling a predetermined quantity of liquid into the syringe cylinder 110; b) putting the syringe needle 141 into the dermis of the skin; c) pulling the piston rod 115 to allow a desired quantity of gas to be supplied to the interior of the syringe cylinder 110 through the inflow passageway 126 of the inflow tube 125, such that the desired quantity of gas exists in the front end portion of the syringe cylinder 110 and the liquid filled into the syringe cylinder 110 is placed below the desired quantity of gas; and d) pushing the piston rod 115 to first inject the desired quantity of gas into the dermis through the outflow check valve 130 and the syringe needle 141 and to then inject a desired quantity of liquid into the dermis through the outflow check valve 130 and the syringe needle 141, wherein the steps c) and d) are repeatedly carried out to allow the gas and liquid to be injected by desired quantities in turn into the dermis.

Thirdly, according to the third embodiment of the present invention as shown in FIG. 3, an operation method using the syringe for treating facial wrinkles includes the steps of: a) filling a predetermined quantity of liquid into the syringe cylinder 1101; b) putting the syringe needle 141 into the dermis of the skin; c) pulling the piston rod 115 to allow a desired quantity of gas to be supplied to the interior of the first syringe cylinder 1103 through the inflow passageway 126 of the inflow tube 125, such that the desired quantity of gas exists in the front end portion of the first syringe cylinder 1103 and the liquid filled into the syringe cylinder 1101 is placed below the desired quantity of gas; and d) pushing the piston rod 115 to first inject the desired quantity of gas into the dermis and to then inject a desired quantity of liquid into the dermis, wherein the steps c) and d) are repeatedly carried out to allow the gas and liquid to be injected by desired quantities in turn into the dermis.

Fourthly, according to the fourth embodiment of the present invention as shown in FIG. 4, an operation method using the syringe for treating facial wrinkles includes the steps of: a) filling a predetermined quantity of liquid into the syringe cylinder 1101; b) putting the syringe needle 141 into the dermis of the skin; c) pulling the piston rod 115 to allow a desired quantity of gas to be supplied to the interior of the first syringe cylinder 1103 through the inflow passageway 126 of the inflow tube 125, such that the desired quantity of gas exists in the front end portion of the first syringe cylinder 1103 and the liquid filled into the syringe cylinder 1101 is placed below the desired quantity of gas; and d) pushing the piston rod 115 to first inject the desired quantity of gas into the dermis through the outflow check valve 130 and the syringe needle 141 and to then inject a desired quantity of liquid into the dermis through the outflow check valve 130 and the syringe needle 141, wherein the steps c) and d) are repeatedly carried out to allow the gas and liquid to be injected by desired quantities in turn into the dermis.

Fifthly, according to the fifth embodiment of the present invention as shown in FIG. 7, an operation method using the syringe for treating facial wrinkles includes the steps of: a) coupling the needle body 1402 to the connection tube 111 of the syringe cylinder 110 or 1101; b) filling a predetermined quantity of liquid into the syringe cylinder 110 or 1101; c) putting the syringe needle 141 into the dermis of the skin; d) pulling the piston rod 115 to allow a desired quantity of gas to be supplied to the interior of the needle body 1402 through the inflow passageway 126 of the inflow tube 125, such that the desired quantity of gas exists in the interior of the needle body 1402 and the liquid filled into the syringe cylinder 110 or 1101 is placed below the desired quantity of gas; and e) pushing the piston rod 115 to first inject the desired quantity of gas into the dermis and to then inject a desired quantity of liquid into the dermis, wherein the steps d) and e) are repeatedly carried out to allow the gas and liquid to be injected by desired quantities in turn into the dermis.

Sixthly, according to the sixth embodiment of the present invention as shown in FIG. 8, an operation method using the syringe for treating facial wrinkles includes the steps of: a) coupling the needle body 1402 to the connection tube 111 of the syringe cylinder 110 or 1101; b) filling a predetermined quantity of liquid into the syringe cylinder 110 or 1101; c) putting the syringe needle 141 into the dermis of the skin; d) pulling the piston rod 115 to allow a desired quantity of gas to be supplied to the interior of the needle body 1402 through the inflow passageway 126 of the inflow tube 125, such that the desired quantity of gas exists in the interior of the needle body 1402 and the liquid filled into the syringe cylinder 110 or 1101 is placed below the desired quantity of gas; and e) pushing the piston rod 115 to first inject the desired quantity of gas into the dermis through the outflow check valve 130 and the syringe needle 141 and to then inject a desired quantity of liquid into the dermis through the outflow check valve 130 and the syringe needle 141, wherein the steps d) and e) are repeatedly carried out to allow the gas and liquid to be injected by desired quantities in turn into the dermis.

Reference numerals 113 and 116, which have not been explained yet, denote a syringe cylinder flange and a rod flange.

As set forth in the foregoing, there is provided the syringe for treating facial wrinkles and the operation method using the syringe wherein a desired quantity of gas supplied through the inflow check valve to the interior of the needle body and a predetermined quantity of liquid filled into the syringe cylinder are injected in turn into the dermis of the skin, such that the three-time tissue regeneration is continuously performed at a time.

The present invention also provides an operation method by using the syringe of the present invention as described in the above detailed description.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The effects of performed with the present syringe are shown in the FIGS. 9-16.

What is claimed is:

1. A syringe for treating facial wrinkles having a syringe cylinder, a needle body detachably mounted at the front end portion of the syringe cylinder and having a syringe needle disposed thereon, and a piston rod disposed inside the syringe cylinder for operating a piston, the syringe comprising:

the syringe cylinder formed of a substantially thin tube having an inside diameter in a range of 2.0 mm to 7.0 mm and containing a predetermined quantity of liquid; and an inflow check valve disposed at one side of the front end portion of the syringe cylinder connected to a gas supply for supplying a predetermined quantity of gas to the interior of the syringe cylinder, wherein during movement of the piston through the syringe cylinder, the syringe is configured to inject the predetermined quantity of gas supplied from the gas supply through the inflow check valve into the dermis of the skin before the predetermined quantity of liquid filled into the syringe cylinder is injected into the dermis of the skin, and wherein the syringe is configured so that movement of the piston through the syringe cylinder is repeatedly carried out.

2. The syringe for treating facial wrinkles according to claim 1, further comprising an outflow check valve disposed between the front end portion of the syringe cylinder and the needle body.

3. The syringe for treating facial wrinkles according to claim 1, wherein the syringe cylinder has another syringe cylinder disposed integrally around an outer periphery thereof in such a manner as to have a larger inside diameter than the syringe cylinder.

4. The syringe for treating facial wrinkles according to claim 2, wherein the syringe cylinder has another syringe cylinder disposed integrally around an outer periphery thereof in such a manner as to have a larger inside diameter than the syringe cylinder.

5. The syringe for treating facial wrinkles according to claim 1, wherein the gas supplied by the gas supply comprises at least one selected from a group consisting of carbonic acid gas and ammonia gas.

* * * * *